United States Patent [19]

Temple, Jr. et al.

[11] 4,451,650
[45] May 29, 1984

[54] PYRIDO[4,3-b][1,4]OXAZINES AND PYRIDO[4,3-b][1,4]THIAZINES

[75] Inventors: Carroll G. Temple, Jr.; John A. Montgomery; Robert D. Elliott; Glynn P. Wheeler, all of Birmingham, Ala.

[73] Assignee: Southern Research Institute, Birmingham, Ala.

[21] Appl. No.: 436,667

[22] Filed: Oct. 26, 1982

[51] Int. Cl.³ .................. C07D 498/04; C07D 513/04
[52] U.S. Cl. .................................... 544/105; 424/246; 424/248.52; 424/248.54; 544/14; 544/48; 544/99
[58] Field of Search ...................... 544/14, 48, 99, 105

[56] References Cited

PUBLICATIONS

Takahashi T., Yoneda F., Chem. Pharm. Bull. (Japan), 1955, 3, 331.
Elion G. B., Hitchings G. H., J. Amer. Chem. Soc., 1952, 74, 3877.
Dunn D. L., Skinner C. G., J. Org. Chem., 1975, 40, 3713.
Lin S.-C., Holmes C. G., Dunn D. L., Skinner C. G., J. Med. Chem., 1979, 22, 741.
Winchester M. J., J. Heterocycl. Chem., 1979, 16, 1455.
Winchester M. J., Zappone L. J., Skinner C. G., J. Heterocycl. Chem., 1981, 18, 455.
Mirza J., Pfleiderer W., Brewer A. D., Stuart A., Wood H. C. S., J. Chem. Soc., C., 1970, 437.
Russell P. B., Elion G. B., Hitchings G. H., J. Amer. Chem. Soc., 1949, 71, 474.
Takahashi T., Maki Y., Chem. Pharm. Bull. (Japan), 1955, 3, 92.
Bojarska-Dahlig J., Piechaczek, J. Chem. Abstracts, 1969, 69 19097h.
Nair M. G., Boyce L. H., Berry M. A., J. Org. Chem., 1981, 46, 3354.

Primary Examiner—Richard Raymond
Attorney, Agent, or Firm—Roylance, Abrams, Berdo & Goodman

[57] ABSTRACT

There are disclosed certain 2H-pyrido[4,3-b][1,4]oxazines and 2H-pyrido[4,3-b][1,4]thiazines which possess biological activity. The compounds have the structure:

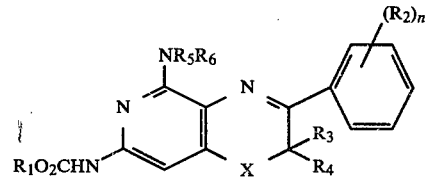

wherein n has a value of 1,2 or 3; X is oxygen or sulfur; $R_1$ is a lower alkyl group, e.g., an alkyl group containing up to six carbon atoms such as methyl, ethyl, propyl, butyl, etc.; $R_2$ is a member selected from the group consisting of hydrogen, alkyl radicals having from about one to about 12 carbon atoms, preferably from about one to about six carbon atoms; alkenyl radicals having from about two to about 15 carbon atoms; preferably from about two to about 10 carbon atoms; cycloalkyl radicals having from about three to about 20 carbon atoms, preferably from about three to about 15 carbon atoms; aryl, aralkyl and alkaryl radicals having from about six to about 20 carbon atoms, preferably from about six to about 15 carbon atoms; a halogen radical, e.g., chlorine, fluorine, bromine and iodine; a hydroxyl group; an amino group; an alkoxy or aryloxy group; a carboxyl group or an alkylcarboxyl group having from about one to about 10 carbon atoms, preferably from about one to about five carbon atoms; an alkythio group or an arylthio group having from about one to about 20 carbon atoms, preferably from about one to about 15 carbon atoms; a sulfonic acid group or alkyl- or arylsulfonyl group having from about one to about 20 carbon atoms, preferably from about one to about 15 carbon atoms; an alkyl- or arylsulfinyl group having from about one to about 20 carbon atoms, preferably from about one to about 15 carbon atoms; an alkyl- or aryl mono- or diamino group having from about one to about 20 carbon atoms, preferably from about one to about 15 carbon atoms; a hydrocarbyl group, such as defined above, carrying halogen, hydroxyl, amino, alkoxy or aryloxy; when taken together with the aromatic ring to which it is attached, a fused ring structure such as naphthyl; and, when taken together with $R_3$, an alkylene radical containing from about one to about 12 carbon atoms, preferably from about one to about six carbon atoms; $R_3$ is hydrogen, methyl, phenyl or, when taken with $R_2$, an alkylene radical as previously defined; $R_4$ is hydrogen or methyl; $R_3$ and $R_4$, when taken together are the radical =O; and $R_5$ and $R_6$ are both hydrogen, or one is hydrogen and the other is the radical

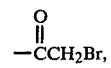

or where taken together are the radical $=CHN(CH_3)_2$.

21 Claims, No Drawings

PYRIDO[4,3-b][1,4]OXAZINES AND PYRIDO[4,3-b][1,4]THIAZINES

BACKGROUND OF THE INVENTION

This invention relates to novel pyrido[4,3-b][1,4]oxazines and pyrido[4,3-b][1,4]thiazines. This invention also relates to processes for making such compounds.

The vinca alkaloids (vincristine and vinblastine) and the podophyllotoxin derivative VP-16 are valuable clinical antitumor agents [De Conti, R. C. and Creasey, W. A., "The catharanthus Alkaloids, Botany, Chemistry, Pharmacology and Clinical Uses", Taylor, W. I. and Farnsworth, N. R., eds., Marcel Dekker, Inc., New York, 1975, p. 237]. These compounds are thought to act primarily by binding with tubulin [Montgomery, J. A., Johnston, T. P., and Shealy, Y. F., in "Burger's Medicinal Chemistry", Wolff, M. E., 4th Edition (Part II), John Wiley and Sons, New York, 1979, p. 635] which causes the accumulation of cells at mitosis. This biological action is similar to that produced by colchicine, griseofulvin, and certain substituted benzimidazoles (e.g., nocodazole) [Atassi, G., Schaus, C., and Tagnon, H. J., Eur. J. Cancer 1975, 11, 609; Debrobander, M. J., Van de Veire, R. M. L., Aerts, F. E. M., Borgers, M., and Janssen, P. A. J., Cancer Res. 1976, 36, 905] and pyrimidines (e.g., 1-propargyl-5-chloropyrimidin-2-one) [Wibe, E. and Oftebro, R., Eur. J. Cancer Clin. Oncol. 1981, 17, 1053].

Recently a number of 1,2-dihydropyrido[3,4-b]pyrazines have been identified as antimitotic inhibitors with antitumor activity against several experimental neoplasms [Temple, C., Jr., Wheeler, G. P., Elliott, R. D., Rose, J. D. Kussner, C. L., Comber, R. N., and Montgomery, J. A., J. Med. Chem. 1982, 25, 1045; Temple, C., Jr., Wheeler, G. P., Elliott, R. D., Rose, J. D., Comber, R. N., and Montgomery, J. A., J. Med. Chem. 1982, 25, in press; Wheeler, G. P., Bowdon, B. J., Werline, J. A., Adamson, D. J., and Temple, C., Jr., Cancer Research 1982, 42, 791; and our copending applications Ser. No. 354,164, filed Mar. 3, 1982 and Ser. No. 362,480, filed Mar. 26, 1982].

The reaction of 3-amino-4-hydroxypyridine with ethyl 2-chloroacetoacetate in a mixture of ethanol and pyridine to give a pyrido[4,3-b][1,4]oxazine is the only example reported for the formation of this ring system [Takahashi, T. and Yoneda, F., Chem. Pharm. Bull (Japan), 1955, 3, 331]. In contrast, several groups have investigated the preparation and evaluation of pyrimido[4,5-b][1,4]oxazines as potential antifolates [Elion, G. B. and Hitchings, G. H., J. Amer. Chem. Soc., 1952, 74, 3877; Dunn, D. L. and Skinner, C. G., J. Org. Chem., 1975, 40, 3713; Lin, S.-C., Holmes, G. P., Dunn, D. L. and Skinner, C. G., J. Med. Chem., 1979, 22, 741; Winchester, M. J., J. Heterocycl. Chem., 1979, 16, 1455; Winchester, M. J., Zappone, L. J., and Skinner, C. G., J. Heterocycl. Chem., 1981, 18, 455]. The formation of pyrimido[4,5-b][1,4]oxazines from polyfunctional pyrimidines (e.g., 2,4,5-triamino-6-hydroxypyrimidine) and alpha-halo carbonyl compounds in a mixture of water and ethanol has been studied in detail by Wood and coworkers [Mirza, J., Pfleiderer, W., Brewer, A. D., Stuart, A., Wood, H. C. S., J. Chem. Soc., C., 1970, 437]. Although these reactants might possibly generate a number of bicyclic ring systems, only dihydropteridines were observed either as a minor or major by-product. Apparently pyrimido[4,5-b][1,4]oxazines are only formed from pyrimidines in which the hydroxy group is conjugated with an electron donating group containing a lone pair of electrons [Mirza, J., Pfleiderer, W., Brewer, A. D., Stuart, A., Wood, H. C. S., J. Chem. Soc., C., 1970, 437; Russell, P. B., Elion, G. B., and Hitchings, G. H., J. Amer. Chem. Soc., 1949, 71, 474].

Two reports have appeared on the alkylation of 4-mercapto-3-nitropyridine with an alpha-halocarbonyl compound followed by the reductive cyclization of the resulting thioether to give a pyrido[4,3-b][1,4]-thiazine [Takahasi, T., and Maki, Y., Chem. Pharm. Bull (Japan), 1955, 3, 92; Bojarska-Dahlig, H., Piechaczek, J., Chem. Abstracts, 1969, 69 19097h]. Also, pyrimido[4,3-b][1,4]thiazines have been prepared by this procedure [Nair, M. G., Boyce, L. H., and Berry, M. A., J. Org. Chem., 1981, 46, 3354] and by treatment of 5-amino-4-mercaptopyrimidines with alpha-halocarbonyl compounds [Mirza, J., Pfleider, W., Brewer, A. D., Stuart, A, Wood, H. C. S., J. Chem. Soc.C., 1970, 437]. Because of the nucleophilicity of sulfur, relative to oxygen, the formation of isomeric ring systems in either the pyrido or pyrimido system has not been encountered.

SUMMARY OF THE INVENTION

It has now been found that certain 2H-pyrido[4,3-b][1,4]oxazines and 2H-pyrido[4,3-b][1,4]thiazines possess biological activity. The compounds of this invention have the structure:

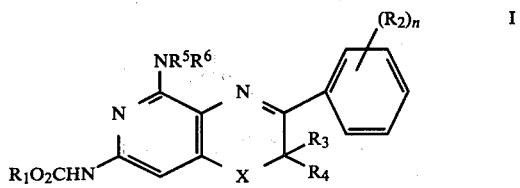

wherein n has a value of 1,2 or 3; X is oxygen or sulfur; $R_1$ is a lower alkyl group, e.g., an alkyl group containing up to six carbon atoms such as methyl, ethyl, propyl, butyl, etc.; $R_2$ is a member selected from the group consisting of hydrogen, alkyl radicals having from about one to about 12 carbon atoms, preferably from about one to about six carbon atoms; alkenyl radicals having from about two to about 15 carbon atoms, preferably from about two to about 10 carbon atoms; cycloalkyl radicals having from about three to about 20 carbon atoms, preferably from about three to about 15 carbon atoms; aryl, aralkyl and alkaryl radicals having from about six to about 20 carbon atoms, preferably from about six to about 15 carbon atoms; a halogen radical, e.g., chlorine, fluorine, bromine and iodine; a hydroxyl group; an amino group; an alkoxy or aryloxy group; a carboxyl group or an alkylcarboxyl group having from about one to about 10 carbon atoms, preferably from about one to about five carbon atoms; an alkylthio group or an arylthio group having from about one to about 20 carbon atoms, preferably from about one to about 15 carbon atoms; a sulfonic acid group or alkyl- or arylsulfonyl group having from about one to about 20 carbon atoms, preferably from about one to about 15 carbon atoms; an alkyl- or arylsulfinyl group having from about one to about 20 carbon atoms, preferably from about one to about 15 carbon atoms; an alkyl- or aryl mono- or diamino group having from about one to about 20 carbon atoms, preferably from about one to about 15 carbon atoms; a hydrocarbyl group, such as defined above, carrying halogen, hydroxyl, amino, alkoxy or aryloxy; when taken together with the aromatic ring to which it is attached, a fused ring structure such as naphthyl; and, when taken together with $R_3$, an alkylene radical containing from about one to about 12 carbon atoms, preferably from about one to about six carbon atoms; $R_3$ is hydrogen, methyl, phenyl or, when taken with $R_2$, an alkylene radical as previously defined; $R_4$ is hydrogen or methyl; $R_3$ and $R_4$, when taken together are the radical =O, and $R_5$ and $R_6$ are both hydrogen, or one is hydrogen and the other is the radical

or when taken together are the radical $=CHN(CH_3)_2$.

DETAILED DESCRIPTION OF THE INVENTION

The compounds of this invention may be prepared from the following intermediates by the reaction sequences shown:

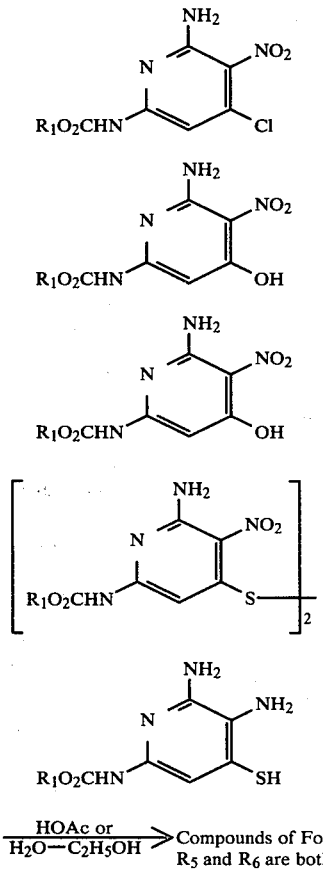

wherein $R_1$ is the same as previously defined.

These reaction sequences are explained as follows:

Hyrolysis of the chloro group of ethyl 6-amino-4-chloro-5-nitropyridin-2-ylcarbamate (II: $R_1=C_2H_5$) with formic acid gave the corresponding 4-hydroxypyridine III ($R_1=C_2H_5$). Catalytic hydrogenation of the nitro group of III ($R_1=C_2H_5$) gave the 5-amino-4-hydroxypyridine IV ($R_1=C_2H_5$), which was reacted with alpha-halo ketones in acetic acid at room temperature to give a series of 3- and 2,3-substituted ethyl 5-aminopyrido[4,3-b][1,4]oxazin-7-ylcarbamates (I: X=oxygen; $R_1=C_2H_5$). Treatment of these compounds with hot concentrated hydrochloric acid regenerated the pyridine synthon IV ($R_1=C_2H_5$). In the reaction of II ($R_1=C_2H_5$) with thioacetate, the product underwent hydrolysis and air oxidation to give the corresponding disulfide V ($R_1=C_2H_5$). Simultaneous reduction of both the nitro group and disulfide linkage of V ($R_1=C_2H_5$) gave the 5-amino-4-mercaptopyridine VI ($R_1=C_2H_5$), which was reacted with alpha-halo ketones either in acetic acid at room temperature or in a mixture of ethanol and water at reflux to give a series of 3-, 2,3-, and 2,2,3-substituted ethyl 5-aminopyrido[4,3=b][1,4]thiazin-7-ylcarbamates (I: X=sulfur; $R_1=C_2H_5$).

It is recognized that intermediates IV and VI can exist as the keto tautomers; however, only the enol tautomer is shown.

The alpha-halo ketones which may be reacted with the compounds of Formulas IV and VI to form compounds as defined by Formula I wherein $R_5$ and $R_6$ are both hydrogen, except where $R_3$ and $R_4$ taken together are the radical =O, have the structure:

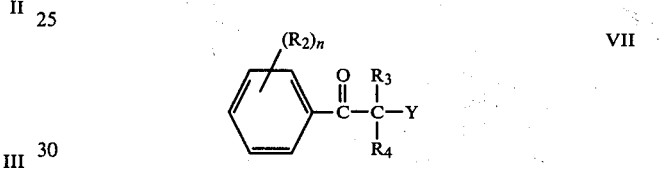

wherein n, $R_2$, $R_3$ and $R_4$ are the same as previously defined and Y is a halogen atom, preferably Br. Compounds of Formula I wherein $R_5$ and $R_6$ are both hydrogen and where $R_3$ and $R_4$ taken together are the radical =O are formed by reacting compounds of Formulas IV or VI with a methyl benzoyl formate having the structure:

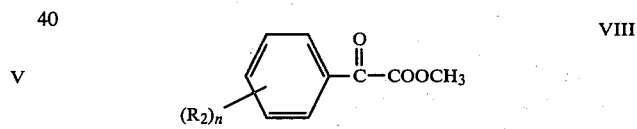

wherein n and $R_2$ are the same as previously defined.

Compounds of Formula I form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Therapeutic compositions containing compounds of Formula I are useful for ameliorating cancer diseases in mammals. The active ingredients of the therapeutic compositions inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

The following examples illustrate the best modes known for carrying out this invention. The alpha-halo ketones and methyl benzoylformate used in the examples were purchased from commercial sources except for 3,4,5-trimethoxy-alpha-bromoacetophenone [Horton, W. J. and Thompson, G., *J. Amer. Chem. Soc.*, 1954, 76, 1909] and 2-bromo-1-tetralone [Barfknecht, C. F., Ruaterholz, D. B., and Parsons, J. A., *J. Med. Chem.*, 1974, 17, 308], which were prepared by bromination of the corresponding ketones. Raney nickel catalyst No. 28 was obtained from W. R. Grace and Co. Melting points were determined with a Mel-Temp apparatus and are uncorrected.

EXAMPLE 1

Ethyl 5,6-Diamino-4-hydroxypyridin-2-ylcarbamate (IV: $R_1=C_2H_5$)

A solution of the nitropyridine (III: $R_1=C_2H_5$) (6.7 g, 28 mmol) [Temple, C., Jr., Smith, B. H., Kussner, C. L., and Montgomery, J. A., *J. Org. Chem.*, 1976, 41, 3748] in a 1:1 mixture of $C_2H_5OH$—$H_2O$ (600 ml) containing Raney nickel (6 g, weighed wet, washed with $H_2O$ then $C_2H_5OH$) was stirred under hydrogen at room temperature and atmospheric pressure until the theoretical volume of hydrogen was absorbed (1.5 hours). The catalyst was removed by filtration (Celite), and the filtrate was acidified with concentrated HCl (2.3 ml) and evaporated to dryness in vacuo. The residue was triturated with $C_2H_5OH$ (50 ml), the mixture was cooled, and the product was collected by filtration and dried in vacuo over $P_2O_5$: yield, 7.0 g (92%); mp ~210° C. with foaming. $^1H$—NMR (DMSO—$d_6$, 5% w/v), $\delta 1.27$ (t, 3, $CH_3$), 4.22 (q, 2, $CH_2$), 6.63 (s, 1.3—CH), 8.56 (br s, NH, $H_2O$), 11.03 (br s, 1H, NH).

Anal. Calcd for $C_8H_{12}N_4P_3 \cdot 1.68$ HCl$\cdot 0.14 H_2O$: C, 34.81; H, 5.09; N, 20.30; Cl, 21.58. Found: C, 34.58; H, 5.02; N, 20.30; Cl, 21.61.

EXAMPLE 2

Diethyl 4,4'-Dithiobis[6-amino-5-nitropyridin-2-ylcarbamate](V: $R_1=C_2H_5$)

A. A solution of the 4-chloropyridine (II: $R_1=C_2H_5$) (2.6 g, 10 mmol) [Elliott, R. D., Temple, C., Jr., and Montgomery, J. A., *J. Org. Chem.*, 1966, 31, 1890] and potassium thioacetate (1.7 g, 15 mmol) in $C_2H_5OH$ (50 ml) was refluxed for 2 hours. The yellow solid that precipitated was collected by filtration, washed with $C_2H_5OH$ (50 ml), and stirred in $H_2O$ (100 ml) for 16 hours. The yellow-orange product was collected by filtration and dried in vacuo: yield, 2.0 g (78%); mp ~255° C. dec. Mass spectrum: m/e 514 (M+). $^1H$—NMR (DMSO—$d_6$, 6% w/v), $\delta 1.18$, 1.20 (t, t, 3, 3, $CH_3$), 4.08, 4.11 (q, q, 2, 2, $CH_2$), 7.66, 7.74 (s, s, 1, 1, 2—CH, 2'—CH), 7.74, 8.14 (br s, br s, 2, 2, $NH_2$), 10.4 s (2H, NH).

Anal. Calcd for $C_{16}H_{18}N_8O_8S_2 \cdot 0.15 C_2H_6O$: C, 37.55, H, 3.65; N, 21.49. Found: C, 37.82; H, 3.81; N, 21.55.

B. A solution of II($R=C_2H_5$) (2.6 g, 10 mmol) and thiourea (3.1 g, 40 mmol) in $C_2H_5OH$ (50 ml) was refluxed under $N_2$ for 5 hours, cooled to 25° C., treated with 1 N NaOH (10 ml, 10.0 mmol) and stirred (exposed to air) at room temperature for 24 hours. The pale green precipitate was collected by filtration, washed with $H_2O$, and heated in refluxing $C_2H_5OH$ (60 ml) to give crude V ($R=C_2H_5$): yield, 2.0 g (~79%). Mass spectrum: m/e 514 (M+).

EXAMPLE 3

Ethyl 5-Amino-3-(4-chlorophenyl)-2H-pyrido-[4,3-b][1,4]oxazin-7-ylcarbamate (I: n=1; X=oxygen; $R_1=C_2H_5$; $R_2=4$—Cl; $R_3=H$; $R_4=H$; $R_5=H$; $R_6=H$)

A solution of III ($R_1=C_2H_5$) (1.0 g, 4.1 mmol) in 1:1 $H_2O$-$C_2H_5OH$ (100 ml) was hydrogenated as described in Example 1 to obtain ethyl 5,6-diamino-4-hydroxypyridin-2-ylcarbamate. The filrate was acidified with 1 N HCl (8.5 ml) and evaporated to dryness in vacuo. A solution of this residue in acetic acid (22 ml) containing alpha-bromo-p-chloroacetophenone (1.0 g, 4.3 mmol) and potassium acetate (1.2 g, 12 mmol) was stirred under $N_2$ at room temperature for 24 hours. The yellow precipitate was collected by filtration, washed with acetic acid (15 ml) and suspended in water (50 ml). This mixture was adjusted to pH 8.5 with 1 N NaOH, and the product was collected by filtration. The reaction time, yield and properties are set forth in Table I in the line designated product h Additional products were prepared similarly wherein the alpha-bromo-p-chloroacetophenone was replaced with the following compounds to make the products designated below:

| Product | Compound |
|---------|----------|
| a | alpha-bromoacetophenone |
| b | alpha-bromopropiophenone |
| c | 2-chloro-2-phenylacetophenone |
| d | 2-bromo-1-tetralone |
| e | methyl benzoylformate |
| f | 3-methoxy-alpha-bromoacetophenone |
| g | 3,4,5-trimethoxy-alpha-bromoacetophenone |
| i | 4-nitro-alpha-bromoacetophenone |

The properties and yield of the products designated a–g and i and the reaction times for forming these products are set forth in Table I. The second column of Table I sets forth the structure of the group:

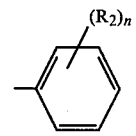

and of the groups $R_3$ and $R_4$ in the products a–i, the formula for which appears in Table I. For products b and d, the ethyl 5,6-diamino-4-hydroxypyridine-2-ylcarbamate was washed with ethanol and dried in vacuo over $P_2O_5$. The yield of product a was increased from 40 to 77% by using a dried sample of ethyl 5,6-diamino-4-hydroxypyridin-2-ylcarbamate.

Cleavage of the oxazine ring of 2H-pyrido[4,-3-b][1,4]oxazines with hydrochloric acid A solution of product a (100 mg, 0.32 mmol) in concentrated HCl (5 ml) was heated at ~100° C. for 48 hours and evaporated to dryness. TLC (7:3 CHCl3:MeOH, 5% HOAc) showed the formation of ethyl 5,6-diamino-4-hydroxypyridin-2-yl-carbamate ($R_f$=0.48). Mass spectrum: m/e 212 (M+). Under similar conditions, products b–i gave ethyl 5,6-diamino-4-hydroxypyridin-2-ylcarbamate. This provided confirmation of the structures.

Further confirmation of the structure of product a, i.e., the presence of an amino group in the 5 position, was provided by the condensation of the product with N,N-dimethylformamide dimethyl acetal to give ethyl 5-(N,N-dimethylamidino)-3-phenyl-2H-pyrido[4,3-b][1,4]oxazin-7-ylcarbamate as set forth in Example 6; and with bromoacetic anhydride to give ethyl 5-[(bromoacetyl)amino]-3-phenyl-2H-pyrido[4,3-b][1,4]oxazin-7-ylcarbamate as set forth in Example 7.

EXAMPLE 4

Ethyl 5-Amino-3-phenyl-2H-pyrido[4,3-b][1,4]-thiazin-7-ylcarbamate (I: X=sulfur; $R_1$=$C_2H_5$; $R_2$=H; $R_3$=H; $R_4$=H; $R_5$=H; $R_6$=H)

To a solution of the disulfide prepared in Example 2 (6.00 g, 11.5 mmol) in acetic acid (240 ml under $N_2$ at 80° C. was added zinc dust (23 g) portionwise over 0.5 hours. After heating the mixture to reflux, then cooling, the insoluble material was removed by filtration and washed with acetic acid (30 ml). The filtrate and wash were combined, evaporated to dryness, and the resulting brownish oil was triturated with an aqueous solution of 0.1 M $KH_2PO_4$ (200 ml) to give the crude zinc salt of the compund of Formula VI ($R_1$=$C_2H_5$) as a light, blue tinted solid: yield, 6.5 g. A portion of this solid (2.0 g) and alpha-bromoacetophenone (3.1 g, 15 mmol) in acetic acid (30 ml) was stirred under $N_2$ for 40 hours. The yellow solid was collected by filtration, washed well with $H_2O$ (50 ml) and $C_2H_5OH$ (50 ml) and dissolved in $CHCl_3$. The solution was applied to a short

TABLE I

Ethyl 5-Amino-2H—pyrido[4,3-b][1,4]oxazin-7-ylcarbamates

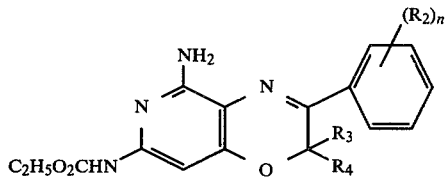

| | | | | | | $^1$H—NMR,[b] | | | Analyses | | | | | |
|---|---|---|---|---|---|---|---|---|---|---|---|---|---|---|
| | | Time, | Yield | | | ring protons | | | Calcd, % | | | Found, % | | |
| Product | | hours | % | M.p. °C. | m/e[a] | 2 | 3 | Formula | C | H | N | C | H | N |
| a, | $C_6H_5$, $R_3$ = $R_4$ = H | 24 | 40 | 191–3 dec. | 312 | 5.20s | 6.67s | $C_{16}H_{16}N_4O_3$.[c] 0.26AcOH 0.5HCl | 57.31 | 5.10 | 16.18 | 57.19 | 5.34 | 16.16 |
| b, | $C_6H_5$, $R_3$ = H, $R_4$ = $CH_3$ | 72 | 21 | 235–8 dec. | 326 | 6.05q | 6.48s | $C_{17}H_{18}N_4O_3$.HCl | 56.28 | 5.28 | 15.44 | 56.34 | 5.41 | 15.36 |
| c, | $C_6H_5$, $R_3$ = $C_6H_5$, $R_4$ = H | 72 | 8 | 187–90 dec. | 388 | 6.65s | 6.77s | $C_{22}H_{20}N_4O_3$.[d] $C_2H_5OH$ | 66.32 | 6.03 | 12.89 | 66.45 | 6.21 | 12.84 |
| d, | $C_6H_4R_2$, $R_2R_3$ = 2-$CH_2CH_2$, $R_4$ = H[e] | 24 | 31 | 248–55 dec. | 338 | 5.13dd | 6.36s | $C_{18}H_{18}N_4O_3$. 1.42HCl | 55.52 | 5.02 | 14.39 | 55.52 | 4.88 | 14.40 |
| e, | $C_6H_5$, $R_3R_4$ = O | 48 | 74 | 205–10[f] | 326 | — | 7.00s | $C_{16}H_{14}N_4O_4$.[d] 0.1$H_2O$ | 58.56 | 4.36 | 17.07 | 58.44 | 4.05 | 17.44 |
| f, | 3-$CH_3OC_6H_4$, $R_3$ = $R_4$ = H | 64 | 52 | 160–3 dec. | 342 | 5.17s | 6.68s | $C_{17}H_{18}N_4O_4$ | 59.64 | 5.30 | 16.37 | 59.99 | 5.62 | 15.99 |
| g, | 3,4,5-$(CH_3O)_3$-$C_6H_2$, $R_3$ = $R_4$ = H | 24 | 70 | 160–3 dec. | 402 | 5.17s | 6.70s | $C_{19}H_{22}N_4O_6$ | 56.71 | 5.51 | 13.92 | 56.39 | 5.51 | 13.92 |
| h, | 4-$ClC_6H_4$, $R_3$ = $R_4$ = H | 24 | 63 | >343 dec. | 346 | 5.17s | 6.69s | $C_{16}H_{15}ClN_4O_3$.[g] 0.23AcOH 0.23$H_2O$ | 54.20 | 4.52 | 15.36 | 54.06 | 4.42 | 15.47 |
| i, | 4-$O_2NC_6H_4$, $R_3$ = $R_4$ = H | 16 | 82 | >300 dec. | 357 | 5.24s | 6.68s | $C_{16}H_{15}N_5O_5$ | 53.78 | 4.23 | 19.60 | 53.95 | 4.51 | 19.40 |

[a]Mass spectra were determined with a Varian MAT 311A spectrometer.
[b] $^1$H—NMR spectra were determined in $(CD_3)_2SO$ solutions with tetramethylsilane as an internal reference with a Varian XL-100-15 spectrometer.
[c] $^1$H—NMR spectrum showed the methyl of the acetate at $\delta$, 1.93.
[d]The presence of solvents was confirmed by the $^1$H—NMR spectra: $H_2O$, $\delta$3.31 br s; $CH_3CH_2OH$, $\delta$1.06 t, 3.45 q.
[e]I.e., this product had the formula

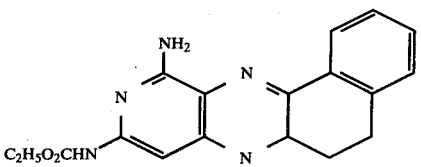

[f]Solidified and remelted at 365–70° C. dec.
[g] $^1$H—NMR spectrum showed the methyl of the acetate at $\delta$1.64 and water $\delta$3.59.

column of EM silica gel 60 (65×35 mm, 230-400 mesh) and eluted with CHCl₃, which retained unreacted zinc salt. The fractions containing product were combined, evaporated to dryness in vacuo, and dried in vacuo: yield, 0.95 g (~40% from the starting sulfide). The reaction time, yield and properties are set forth in Table II in the line designated product j.

EXAMPLE 5

Ethyl 5-Amino-2-methyl-3-phenyl-2H-pyrido[4,-3-b][1,4]thiazin-7-ylcarbamate (I: X=sulfur; $R_1=C_2H_5$; $R_2=H$; $R_3=H$; $R_4=CH_3$; $R_5=H$; $R_6=H$)

The zinc salt (2.0 g), prepared as described in Example 4 was dissolved in $H_2O$ (12 ml) and a solution of alpha-bromopropiophenone (3.4 g, 15 mmol) in $C_2H_5OH$ (12 ml) was added with stirring over 5 minutes. The resulting solution was refluxed for one hour, and evaporated to dryness in vacuo. The dried residue

| Product | Method of Example | Ketone |
|---|---|---|
| o | 4 | alpha-bromo-2'-acetonaphthone |

The properties and yield of the products designated l–o and the reaction times for forming these products are set forth in Table II. The second column of Table II sets forth the structure of the group:

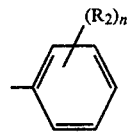

and of the groups $R_3$ and $R_4$ in the products j–o, the formula for which appears in Table II.

TABLE II

Ethyl 5-Amino-2H—pyrido[4,3-b][1,4]thiazin-7-ylcarbamates

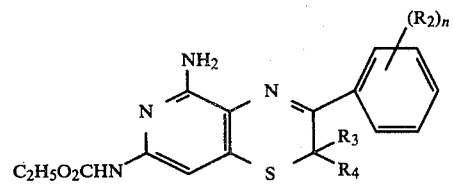

| | | | | | ¹H—NMR,[b] ring protons | | | Analyses Calcd, % | | | Found, % | | |
|---|---|---|---|---|---|---|---|---|---|---|---|---|---|
| Product | Time, Hours | Yield % | M.p. °C. | m/e[a] | 2 | 8 | Formula | C | H | N | C | H | N |
| j, $C_6H_5$, $R_3 = R_4 = H$ | 40 | 40 | 197–9 dec. | 328 | 3.88(s) | 7.04(s) | $C_{16}H_{16}N_4O_2S$.[c] 0.09CHCl₃. 0.33H₂O | 56.00 | 4.89 | 16.24 | 55.89 | 4.86 | 16.29 |
| k, $C_6H_5$, $R_3 = H$, $R_4 = CH_3$ | 1 | 35 | >214 dec. | 342 | 4.94 | 6.80(s) | $C_{17}H_{18}N_4O_2S$. 0.4$C_2H_5OH$ HCl | 53.81 | 5.43 | 14.10 | 53.52 | 5.54 | 14.10 |
| l, $C_6H_5$, $R_3 = R_4 = CH_3$ | 8 | 25 | 170–2 dec. | 356 | — | 6.78(s) | $C_{18}H_{20}N_4O_2S$.HCl | 55.02 | 5.39 | 14.26 | 55.20 | 5.58 | 14.31 |
| m, 3-$CH_3OC_6H_4$, $R_3 = R_4 = H$ | 48 | 27 | 169–73 | 358 | 3.87(s) | 7.04(s) | $C_{17}H_{18}N_4O_3S$ | 56.97 | 5.06 | 15.63 | 56.90 | 5.47 | 15.95 |
| n, 4-$CH_3OC_6H_4$, $R_3 = R_4 = H$ | 60 | 28 | 194–6 dec. | 358 | 3.84(s) | 7.03(s) | $C_{17}H_{18}N_4O_3S$.[c] 0.05CHCl₃ | 56.20 | 5.00 | 15.37 | 55.99 | 5.36 | 15.28 |
| o, 2-$C_{10}H_7$, $R_3 = R_4 = H$ | 40 | 40 | 174–7 dec. | 378 | 4.04(s) | 7.08(s) | $C_{20}H_{18}N_4O_2S$ | 63.47 | 4.79 | 14.80 | 63.36 | 4.98 | 14.78 |

[a]Mass spectra were determined with a Varian MAT 311A spectrometer.
[b] ¹H—NMR spectra were determined in $(CD_3)_2SO$ solutions with tetramethylsilane as internal references with a Varian XL-200-15 spectrometer.
[c]The presence of solvents was confirmed by the ¹H—NMR spectra: H₂O, δ3.31 br s; CH₃CH₂OH, δ1.06 t, 3.45 q; CHCl₃, δ8.31.

was dissolved in CHCl₃ and eluted from a short column of EM silica gel 60 (65×40 mm, 230–400 mesh) with CHCl₃. The fractions containing product were combined and evaporated to dryness in vacuo. The residue was dissolved in $C_2H_5OH$ and acidified with concentrated HCl (0.25 ml) to precipitate the hydrochloride: yield, 0.85 g. The reaction time, yield and properties are set forth in Table II in the line designated product k.

Additional compounds were prepared by the method of Examples 4 or 5, as indicated below, wherein the ketone used in those examples was replaced with the following ketones to make the products designated below:

| Product | Method of Example | Ketone |
|---|---|---|
| l | 5 | alpha-bromoisobutyrophenone |
| m | 4 | 3-methoxy-alpha-bromoacetophenone |
| n | 4 | 4-methoxy-alpha-bromoacetophenone |

EXAMPLE 6

Ethyl 5-(N,N-Dimethylamidino)-3-phenyl-2H-pyrido[4,3-b][1,4]oxazin-7-ylcarbamate (I: X=oxygen; $R_1=C_2H_5$; $R_2=H$; $R_3=H$; $R_4=H$; $R_5R_6=CHN(CH_3)_2$)

A solution of product a obtained in Example 3 (165 mg, 0.530 mmol) and N,N-dimethylformamide dimethylacetal (630 mg, 5.30 mmol) in N,N-dimethylformamide (4 ml) was stirred under $N_2$ at room temperature for 24 hours. The solvent was removed in vacuo on a warm water bath at 35° C., and the resulting semi-crystalline yellow residue was triturated with ethyl ether and collected by filtration: yield, 100 mg (52%); mp=158°–161° C. Mass spectrum; m/e 367 (M)⁺. ¹H—NMR (CDCl₃), 3.75% w/v) δ 1.30 t (3H, OCH₂CH₃); 3.10 s (3H, N—CH₃); 3.19 s (3H, N—CH₃); 4.23 q (2H, OCH₂CH₃); 5.04 s (2H, 2—CH₂); 7.21 br. s. (1H, NHCO₂); 7.20 s (1H, 8—CH); 7.44 m (3H, aromatic CH's); 7.91 m (2H, aromatic CH's); 8.28 s (1H, CHN(CH$_3$)$_2$).

Anal. Calcd for C$_{19}$H$_{21}$N$_5$O$_3$: C, 62.11; H, 5.76; N, 19.06. Found: C, 62.05; H, 6.05; N, 18.94.

EXAMPLE 7

Ethyl 5-[(Bromoacetyl)amino]-3-phenyl-2H-pyrido[4,3-b][1,4]oxazin-7-ylcarbamate (I: X=oxygen; R$_1$=C$_2$H$_5$; R$_2$=H; R$_3$=H; R$_4$=H; R$_5$=H;

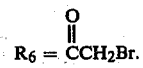

A heterogeneous slurry of bromoacetic anhydride (7 g) and product a obtained in Example 3 (350 mg, 1.12 mmol) was heated at about 50° C. for 2 hours. The cooled solution was diluted to twice its volume with anhydrous ether and stirred for 5 minutes. The hydrobromide was collected by filtration (450 mg), suspended in H$_2$O (50 ml), and adjusted to pH 7 with 1 N NaOH. The solid was collected by filtration, washed with H$_2$O (15 ml) and dried. An incomplete solution of this material (340 mg) in CHCl$_3$ was eluted with CHCl$_3$ from a short column of EM silica gel 60 (32×35 mm, 230-400 mesh). The fractions containing product were evaporated to give a light yellow solid: yield, 200 mg (41%), mp=>230° C. with dec. $^1$H—NMR (CF$_3$COOD, 5% w/v) δ 1.45 t (3H, OCH$_2$CH$_3$); 4.36 s (2H, —CH$_2$BR); 4.49 q (2H, OCH$_2$CH$_3$); 5.63 s (2H, 2—CH$_2$); 6.65 s (1H, 8—CH); 7.63 m, 8.0 m (3H, 2H, aromatic CH's).

Anal. Calcd for C$_{18}$H$_{17}$BrN$_4$O$_4$·0.4H$_2$O: C, 49.08; H, 4.07; N, 12.72; Br, 18.14. Found: C, 49.31; H, 4.29; N, 12.72; Br, 18.03.

Table III sets forth biological data for the pyrido[4,3-b][1,4]oxazines and pyrido[4,3-b][1,4]thiazines of this invention. Products a–i are those set forth in Table I; products j–o are those set forth in Table II; and products p and q are those set forth in Examples 6 and 7, respectively.

TABLE III

Biological Data:
Ethyl 5-Amino-2H—pyrido[4,3-b][1,4]oxazin-7-ylcarbamates and Ethyl 5-Amino-2H—pyrido[4,3-b][1,4]thiazin-7-ylcarbamates

| Product | L1210[a] ID$_{50}$, μM | L1210[b] MI$_{0.5}$ (μM) | P388[c]10$^6$Tumor cell implant, i.p. Schedule | % ILS(mg/kg)[d] |
|---|---|---|---|---|
| a | 0.225 | 0.56 | 1-5 | 44(100) 80(200)[e] |
| b | 0.11 | 0.49 | 1-5 | 50(100) |
| c | 0.88 | 3.0 | 1-5 | 2(200) |
| d | >0.3 | — | 1-5 | 32(300) |
| e | >3 | — | 1-5 | 0(300) |
| f | 0.052 | 0.10 | 1-5 | 73(50)[f] |
| g | >3 | — | 1-5 | 0(300) |
| h | >3 | — | 1-5 | 0(300)[f] |
| i | >3 | — | 1-5 | 0(300) |
| j | 6.1 | 10 | 1-5 | 0(300) |
| k | 1.6 | 9.6 | 1-5 | 10(150) |
| l | >10 | — | — | — |
| m | 0.53 | 2.0 | 1-5 | 3(75) |
| n | 0.34 | 4.9 | 1-5 | 3(300) |
| o | 0.58 | 3.0 | 1-5 | 5(300) |
| p | 0.31 | 0.78 | — | — |
| q | 2.2 | 11 | — | — |

[a]Concentration of agent that inhibits proliferation of cultured lymphoid leukemia L1210 cells to 50% control growth during 48 hours [Wheeler, G. P., Bowdon, B. J., Werline, J. A., Adamson, D. J., and Temple, C., Jr., Cancer Research, 1982, 42, 791].
[b]Concentration of agent that causes a mitotic index (fraction of cells in mitosis divided by total cells) of 0.5 for cultured lymphoid leukemia L1210 cells during an exposure period of 12 hours [Wheeler, G. P., Bowden, B. J., Werline, J. A., Adamson, D. J., and Temple, C., Jr., Cancer Research, 1982, 42, 791].
[c]Lymphocytic leukemia P388.
[d]Increase in life span at the highest nontoxic dose.
[e]Toxic by weight change at a dose of 400 mg/kg.
[f]Toxic by weight change at this dose.

The data in Table III shows that certain pyrido[4,3-b][1,4]oxazines and pyrido[4,3-b][1,4]thiazines of this invention inhibit cell growth, cause mitotic arrest, and are active against leukemia in laboratory animals.

What is claimed is:

1. 2H-Pyrido[4,3-b][1,4]oxazines and 2H-pyrido[4,3-b][1,4]thiazines having the formula:

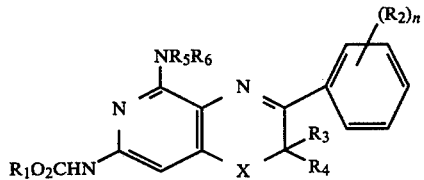

wherein n has a value of 1, 2 or 3; X is oxygen or sulfur; R$_1$ is a lower alkyl group; R$_2$ is a member selected from the group consisting of hydrogen, alkyl radicals having from about one to about 12 carbon atoms; alkenyl radicals having from about two to about 15 carbon atoms; cycloalkyl radicals having from about three to about 20 carbon atoms; aryl, aralkyl and alkaryl radicals having from about six to about 20 carbon atoms; a halogen radical; a hydroxyl group; an amino group; an alkoxy or aryloxy group, a carboxyl group or an alkylcarboxyl group having from about one to about 10 carbon atoms; an alkylthio group or an arylthio group having from about one to about 20 carbon atoms; a sulfonic acid group or alkyl- or arylsulfonyl group having from about one to about 20 carbon atoms; an alkyl- or arylsulfinyl group having from about one to about 20 carbon atoms; an alkyl- or aryl mono- or diamino group having froom about one to about 20 carbon atoms; a hydrocarbyl group as defined above carrying halogen, hydroxyl, amino, alkoxy or aryloxy; nitro; when taken together with the aromatic ring to which it is attached, a fused ring structure; and, when taken together with R$_3$, an alkylene radical containing from about one to about 12 carbon atoms; R$_3$ is hydrogen, methyl, phenyl or, when taken with R$_2$, an alkylene radical as previously defined; R$_4$ is hydrogen or methyl; R$_3$ and R$_4$, when taken together are the radical =O; and R$_5$ and R$_6$ are both hydrogen, or one is hydrogen and the other is the radical

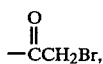

or when taken together are the radical =CHN(CH$_3$)$_2$.

2. A compound as defined in claim 1 wherein R$_1$ is ethyl and R$_5$ and R$_6$ are both hydrogen.

3. A compound as defined in claim 2 wherein X is oxygen.

4. A compound as defined in claim 3 wherein R$_2$, R$_3$ and R$_4$ are all hydrogen.

5. A compound as defined in claim 3 wherein R$_2$ and R$_3$ are each hydrogen and R$_4$ is methyl.

6. A compound as defined in claim 3 wherein R$_2$ is hydrogen, R$_3$ is phenyl and R$_4$ is hydrogen.

7. A compound as defined in claim 3 wherein R$_2$ and R$_3$ taken together comprise the group 2—CH$_2$CH$_2$ and R$_4$ is hydrogen.

8. A compound as defined in claim 3 wherein R$_2$ is hydrogen and R$_3$ and R$_4$ taken together are the group =O.

9. A compound as defined in claim 3 wherein R$_2$ and the phenyl ring to which it is attached is the group 3—CH$_3$OC$_6$H$_4$ and R$_3$ and R$_4$ are each hydrogen.

10. A compound as defined in claim 3 wherein R$_2$ and the phenyl ring to which it is attached is the group 3,4,5—(CH$_3$O)$_3$C$_6$H$_2$ and R$_3$ and R$_4$ are each hydrogen.

11. A compound as defined in claim 3 wherein R$_2$ and the phenyl ring to which it is attached is the group 4—ClC$_6$H$_4$ and R$_3$ and R$_4$ are each hydrogen.

12. A compound as defined in claim 3 wherein R$_2$ and the phenyl ring to which it is attached is the group 4—O$_2$NC$_6$H$_4$ and R$_3$ and R$_4$ are each hydrogen.

13. A compound as defined in claim 2 wherein X is sulfur.

14. A compound as defined in claim 13 wherein R$_2$, R$_3$ and R$_4$ are each hydrogen.

15. A compound as defined in claim 13 wherein R$_2$ and R$_3$ are each hydrogen and R$_4$ is methyl.

16. A compound as defined in claim 13 wherein R$_2$ is hydrogen and R$_3$ and R$_4$ are each methyl.

17. A compound as defined in claim 13 wherein R$_2$ and the phenyl ring to which it is attached is the group 3—CH$_3$OC$_6$H$_4$ and R$_3$ and R$_4$ are each hydrogen.

18. A compound as defined in claim 13 wherein R$_2$ and the phenyl ring to which it is attached is the group 4—CH$_3$OC$_6$H$_4$ and R$_3$ and R$_4$ are each hydrogen.

19. A compound as defined in claim 13 wherein R$_2$ and the phenyl ring to which it is attached is the naphthyl group and R$_3$ and R$_4$ are each hydrogen.

20. Ethyl 5-(N,N-Dimethylamidino)-3-phenyl-2H-pyrido[4,3-b][1,4]oxazin-7-ylcarbamate.

21. Ethyl 5-[(Bromoacetyl)amino]-3-phenyl-2H-pyrido[4,3-b][1,4]oxazin-7-ylcarbamate.

* * * * *